United States Patent
Gallen et al.

(10) Patent No.: US 10,968,157 B2
(45) Date of Patent: *Apr. 6, 2021

(54) PROCESS FOR THE SEPARATION OF FORMALDEHYDE FROM CRUDE ACRYLIC ACID

(71) Applicant: JOHNSON MATTHEY DAVY TECHNOLOGIES LIMITED, London (GB)

(72) Inventors: Robert Gallen, London (GB); Michael William Marshall Tuck, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,444

(22) PCT Filed: Dec. 20, 2017

(86) PCT No.: PCT/GB2017/053843
§ 371 (c)(1),
(2) Date: Jun. 21, 2019

(87) PCT Pub. No.: WO2018/115873
PCT Pub. Date: Jun. 28, 2018

(65) Prior Publication Data
US 2020/0299217 A1    Sep. 24, 2020

(30) Foreign Application Priority Data
Dec. 22, 2016 (GB) .................... 1621985

(51) Int. Cl.
*C07C 45/83* (2006.01)
*C07C 51/44* (2006.01)

(52) U.S. Cl.
CPC .................. *C07C 45/83* (2013.01)

(58) Field of Classification Search
CPC ........ C07C 45/83; C07C 51/353; C07C 51/44
See application file for complete search history.

(56) References Cited

U.S. PATENT DOCUMENTS

| | | | |
|---|---|---|---|
| 3,781,193 A | 12/1973 | Sennewald et al. | |
| 5,160,412 A | 11/1992 | Berg | |
| 6,478,929 B1 | 11/2002 | Parten | |
| 7,393,976 B2 | 7/2008 | Benderly et al. | |
| 8,242,308 B2 | 8/2012 | Ho et al. | |
| 8,536,368 B2 | 9/2013 | Mueller et al. | |
| 8,642,498 B2 | 2/2014 | Nagaki et al. | |
| 8,652,988 B2 | 2/2014 | Nagaki et al. | |
| 8,652,989 B2 | 2/2014 | Sato et al. | |
| 8,658,822 B2 | 2/2014 | Mueller et al. | |
| 8,658,823 B2 | 2/2014 | Peterson et al. | |
| 8,658,824 B2 | 2/2014 | Peterson et al. | |
| 8,729,299 B2 | 5/2014 | Mueller et al. | |
| 8,735,314 B2 | 5/2014 | Nagaki et al. | |
| 8,765,629 B2 | 7/2014 | Norman et al. | |
| 8,864,950 B2 | 10/2014 | Peterson et al. | |
| 8,877,966 B2 | 11/2014 | Herzog et al. | |
| 8,889,586 B2 | 11/2014 | Nagaki et al. | |
| 9,073,846 B2 | 7/2015 | Nagaki et al. | |
| 2013/0267737 A1 | 10/2013 | Mueller et al. | |
| 2013/0317254 A1 | 11/2013 | Kotsianis et al. | |
| 2014/0151112 A1 | 6/2014 | Makino et al. | |
| 2014/0277384 A1 | 9/2014 | Melsheimer | |
| 2014/0277414 A1 | 9/2014 | Kheradvar | |
| 2014/0343318 A1 | 11/2014 | Gruene et al. | |
| 2014/0343319 A1 | 11/2014 | Goebel et al. | |
| 2014/0364644 A1 | 12/2014 | Nagaki et al. | |
| 2017/0129841 A1 | 5/2017 | Hartmann et al. | |

FOREIGN PATENT DOCUMENTS

DE  102015222180 A1  5/2016
WO  WO 86/00236 A1  1/1986

OTHER PUBLICATIONS

GB1621985.9, Search Report Under Section 17(5) dated Aug. 10, 2017.
GB1721494.1, Combined Search and Examination Report Under Section 17 and 18(3), dated Sep. 3, 2019.
PCT/GB2017/053843 (WO2018/115873) International Search Report dated Mar. 2, 2018.
PCT/GB2017/053843 (WO2018/115873) Written Opinion dated Mar. 2, 2018.
Mamoru Ai, "Vapor-Phase Aldol Condensation of Formaldehyde With Aceteic Acid on V2O5-P2O5 Catalysts," Journal of Catalysis, vol. 107, Issue 1, Sep. 1987, pp. 201-208.

*Primary Examiner* — Sikarl A Witherspoon
(74) *Attorney, Agent, or Firm* — BakerHostetler

(57) ABSTRACT

A process for purification of a crude product stream recovered from the production of acrylic acid by an aldolisation reaction is disclosed. The product stream comprises acrylic acid, formaldehyde, water, non-condensable vapours and optionally heavy by-products. The process comprises: providing the crude product stream in the vapour phase to a first separation column operated at a temperature and pressure to form an intermediate overhead stream comprising water, formaldehyde and methanol; and passing said intermediate overhead stream to a formaldehyde separation column operated at a temperature and pressure to enable a stream having a higher formaldehyde concentration than the formaldehyde concentration in the intermediate overhead stream to be formed and recovered from at or near the bottom of the formaldehyde separation column as a formaldehyde enriched stream.

6 Claims, 2 Drawing Sheets

PROCESS FOR THE SEPARATION OF FORMALDEHYDE FROM CRUDE ACRYLIC ACID

CROSS-REFERENCE TO RELATED APPLICATIONS

Figure 1:
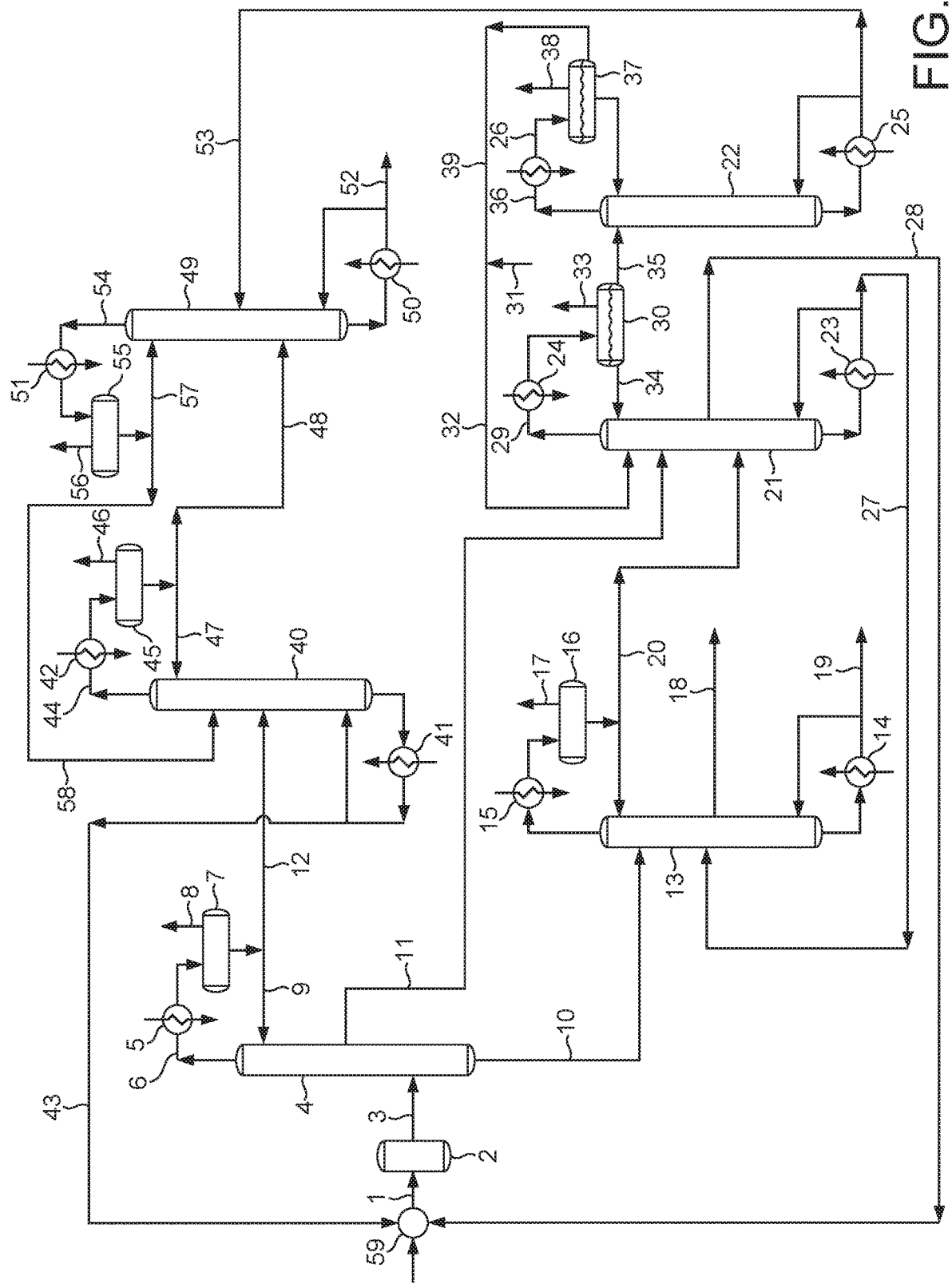

This application is the National Stage of International Patent Application No. PCT/GB2017/053843, filed Dec. 20, 2017, which claims priority to Great Britain Patent Application No. 1621985.9, filed Dec. 22, 2016, the entire disclosures of both of which are incorporated herein by reference for any and all purposes.

The present invention relates to a process for separating an unsaturated carboxylic acid from a product stream produced by an aldol condensation reaction. More particularly, it relates to a process for separating unsaturated carboxylic acid from a crude product stream of a reaction of formaldehyde with a carboxylic acid having one fewer carbon atoms that the desired unsaturated carboxylic acid. Still more particularly, it relates to a process for separating acrylic acid from a product stream produced by the aldol condensation of formaldehyde and acetic acid.

Commercial processes for the production of acrylic acid have relied on the gas phase oxidation of propylene, via acrolein, to form acrylic acid. Whilst the process may be effective, the oxidation reaction is highly exothermic and therefore creates an explosion risk. To minimise the risk, more expensive reactor designs and more expensive metallurgy are required. In addition, the cost of the propylene starting material is generally high which adversely affects the economics of the process. In addition, the supply of the propylene can be insecure and limited.

Alternative routes to acrylic acid have therefore been investigated. One route which has gained interest is the aldol condensation reaction of formaldehyde with acetic acid. This aldol condensation, which takes place over a vanadium oxide-phosphorus oxide catalyst, has been described in Mamoru Ai, Vapor-Phase Aldol Condensation of Formaldehyde with Acetic Acid on $V_2O_5$—$P_2O_5$ Catalysts, Journal of Catalysis 107, 201-208, 1987. The main benefit of the route is the use of feedstock for acrylic acid away from propylene to other sources of carbon.

One example of a process for producing acrylic acids and acrylates by reacting formaldehyde and acetic acid is described in U.S. Pat. No. 8,658,822. In the process described in U.S. Pat. No. 8,658,822, the alkylenating agent, namely formaldehyde, is used in excess relative to the stoichiometric amount of alkanoic acid, namely acetic acid. In particular, a formaldehyde to acetic acid molar ratio of between 1 and 10, and preferably between 1.16 and 1.9 is described. A stoichiometric excess of alkanoic acid relative to alkylenating agent is suggested to be desired in order to improve acrylate selectivity. The process described may optionally also include water, oxygen, and methanol.

It is known that aldol condensation reactions, such as those described in U.S. Pat. No. 8,658,822, are not limited to the use of formaldehyde as the alkylenating agents. For example, it is known that trioxane may also be used as an alkylenating agent and a process similar to that of U.S. Pat. No. 8,658,822, which uses trioxane instead of formaldehyde is described in U.S. Pat. No. 8,536,368.

Formaldehyde or other alkylenating agents, such as trioxane, are generally used in stoichiometric excess relative to acetic acid in order to improve acrylate selectivity. For example, in the processes described in U.S. Pat. Nos. 8,658,822, 8,658,824, 8,889,586, U.S. Ser. No. 14/277,414 and the Mamoru Ai journal article an excess of formaldehyde is preferable as this leads to improved acrylate selectivity. For example, in the process described in U.S. Pat. No. 8,658,824 describes that improved acrylate selectivity is achieved when a stoichiometric excess of formaldehyde relative to acetic acid is used.

Various catalysts have been investigated in relation to their use in aldol condensation reactions. Examples of suitable catalysts are described in U.S. Pat. Nos. 8,642,498, 8,652,988, 8,735,314, 8,877,966, US2014/277384 and U.S. Pat. No. 8,765,629.

However, there are certain disadvantages associated with the use of some known catalysts, particularly vanadium-phosphorus-oxide catalysts. In particular, that they show a tendency to low selectivity of the desired acrylic acid or acrylate at low alkanoic acid to alkylenating agent ratios. This low selectivity reduces the commercial attractiveness of using low alkanoic acid to alkylenating agent ratios as some of the feedstock is lost into an unrecoverable form.

Higher acrylate product selectivity may be achieved by increasing the ratio of high alkanoic acid to alkylenating agent. For example, as described in U.S. Pat. No. 8,658,823 a high alkanoic acid to alkylenating agent ratio can result in an improvement in selectivity to the desired product.

In contrast, some advantages may be demonstrated where the process is operated at low alkanoic acid to alkylenating agent ratio as improved acetic acid conversion may be demonstrated. One example of a process of this type is described in U.S. Pat. No. 8,658,822. However, both selectivity to acrylate product and the space time yield are poor at low alkanoic acid to alkylenating agent ratios.

Without being bound by any theory, it is believed that the differences in selectivity at different ratios of alkanoic acid to alkylenating agent is caused by an inherent property of the catalysts used, either in the proportion of active sites on the catalyst or in the absorptivity of the reactants onto the active sites. For example, where the composition of the reaction feed is stoichiometric, that is where the molar ratio of formaldehyde to acetic acid is one, the concentration of formaldehyde on the catalyst surface may be much greater than that of the acetic acid. This is believed to result in a greater selectivity to carbon oxides and more rapid deactivation of the catalyst. This may be the reason why better formaldehyde conversion and acrylate product selectivity is seen at a molar ratio in excess of 2:1 acid to alkenyating agent, such as formaldehyde.

Various attempts have been made to improve the process. For example, it is suggested in U.S. Pat. No. 8,729,299 that nitrogen can be used as a diluent and that the presence of an oxygen composition may improve catalyst life. Oxygen is also used in the process described in US2013/267737. In this process, it is suggested that a plurality of oxygen streams may assist in the control of selectivity and activity.

Although there has been little change in suggested reaction conditions, there has been a suggestion in US2014/343319 that improved kinetic properties may be achieved at elevated partial pressure of formaldehyde.

There have however been some investigations into suitable catalysts. In U.S. Pat. Nos. 8,642,498 and 8,652,989 a vanadium-titanium-phosphorous oxide is suggested while in U.S. Pat. No. 8,735,314 describes a catalyst formulation comprising vanadium, titanium, ethylene glycol and citric acid. A multi-metal oxide catalyst of vanadium, phosphorous, iron with one of molybdenum, bismuth, cobalt, nickel, silicon, zinc, hafnium, zirconium, titanium, chromium, manganese, copper, boron, tin and niobium and one of lithium, potassium, sodium, rubidium, caesium and thallium.

It has also been suggested, such as in US2014/343318, that improved catalyst performance may be noted where the average oxidation state of vanadium within the catalyst is between +4.4 and +5.

Binary vanadium-titanium phosphate catalysts have also been studied. However, the conversion and selectivity noted in the reaction of acetic acid with formaldehyde are lower than desired. Vanadyl pyrophosphate catalysts have also been extensively studied both alone and in combination with other phosphates such as titanium pyrophosphates. While several studies have shown that vanadium-titanium-phosphorous ternary oxides may demonstrate good catalytic performance in the aldol condensation of acetic acid, with methanol and formaldehyde, $TiO_2$, $V_2O_5$—$TiO_2$, and $TiO_2$—$P_2O_5$ were not found to be as effective.

Despite enjoying a feedstock cost advantage over alternative methods for producing acrylic acid, the process for producing acrylic acid via the aldol condensation of formaldehyde and acetic acid has yet to be commercialised. This is also despite the demand for acrylic acid rising in recent years. The reasons for this failure are considered to be twofold. First is the uncommercial performance of known catalysts as described above and second is the expense and difficulty of the separation process.

In this connection, it will be understood that following the aldol condensation, it is necessary to separate the desired product, such as acrylic acid, from the reaction mixture. Where the process relates to the formation of acrylic acid, the reaction product of the aldol condensation reaction is generally a mixture of at least formaldehyde, water, acrylic acid and acetic acid. In the case where an excess of acetic acid is used, the excess acetic acid remains unreacted, even if complete formaldehyde conversion is achieved. This leads to problems in the separation step particularly as all of the component pairings display non-ideal behaviour. The problematic pairings in the production of acrylic acid include water and formaldehyde, acetic acid and water, and acrylic acid and acetic acid.

A further problem is that since acrylic acid is a heavier component than acetic acid, water, or formaldehyde, distillation as a means of separation will require high energy input. The greater the excess of acid used in the reaction, the greater the impact of this step.

Similar problems are noted with other aldol condensation reactions for the production of unsaturated carboxylic acids.

The separation of this mixture has proven to be challenging and various proposals have been made to try to address the difficulties associated with this separation.

One proposed option is the use of extractive or azeotropic distillation to try to improve the economics of the water-acetic acid separation. Examples of these distillation techniques are given in U.S. Pat. No. 5,160,412, which also describes the use of entrainers, such as isopropyl acetate, to assist in this separation.

Other extraction and separation techniques are described in U.S. Pat. Nos. 8,658,824, 7,393,976, US2013/0317254.

Liquid-liquid extraction has also been investigated. The use of liquid-liquid extraction to separate the acrylate from the alkylenating agent and water is described in US2013/334545. However, a suitably selective solvent has yet to be found.

A particular difficulty of the separation is the tendency of acrylates to polymerise during the separation process such as during distillation and to cause fouling. It is conventional to rely on the addition of inhibitors to reduce or eliminate polymerisation of acrylates. For example, it is suggested in U.S. Pat. No. 8,242,308 that various compounds are known inhibitors of reactions of acrylic acid. Examples of such compounds, including soluble manganese ions, soluble copper ions, and 2,2,6,6-tetramethyl-1-piperidinyloxy are provided.

Another approach to reducing or eliminating polymerisation of acrylates is discussed in U.S. Pat. No. 8,864,950 which describes how maintaining the temperature of the acrylate containing streams to below 140° C. inhibits or eliminates polymerisation. This is achieved by operating the separating columns at low pressures, for example below 20 kPa.

It has also been suggested that employing fewer theoretical stages can also reduce polymerisation. For example, in US2014/151112 it is described how having fewer trays inhibits or eliminates acrylate polymerization.

A further problem is that the crude product stream from the aldol reaction will, in addition to containing the unsaturated carboxylic acid, the corresponding saturated carboxylic acid, the aldehyde such as formaldehyde and water, generally also contain nitrogen, oxygen and heavy by-products of the reaction. Where the reaction is the production of acrylic acid from acetic acid and formaldehyde the by-products may include one or more of acetone, methyl acetate and maleic acid. It is desirable to remove these by-products as their presence may be detrimental to downstream processes.

The presence of these by-products mean that separation schemes used for separating unsaturated carboxylic acid from a crude product stream made by the gas phase oxidation of propylene are not suitable.

Various proposals have been made in an attempt to find a suitable separation scheme. One arrangement is discussed in U.S. Pat. No. 9,073,846. Whilst this process may address some of the problems identified above, the costs of operating the separation are significantly higher than those incurred with conventional schemes such that the economic benefits obtained by carrying out the reaction via the aldol condensation route are consumed. The process also does not address the removal of the heavy by-products.

It is therefore desirable to provide a process which enables unsaturated carboxylic acids, such as acrylic acid, to be separated from a crude product stream comprising the unsaturated carboxylic acid which addresses and preferably overcomes at least one and preferably more than one of the disadvantages and drawbacks of the prior art processes.

It has surprisingly been found that particular benefits can be achieved where the separation process includes a stage in which formaldehyde is separated from a stream comprising water and formaldehyde using a pressure swing system. The recovered formaldehyde is then available to be recovered to a reactor in which the acrylic acid is formed. This may be directly or via intermediate steps.

Thus according to the present invention, there is provided, a process for purification of a crude product stream recovered from the production of acrylic acid by an aldolisation reaction, said product stream comprising acrylic acid, formaldehyde, water, non-condensable vapours and optionally heavy by-products; said process comprising:

(a) providing the crude product stream in the vapour phase to a first separation column operated at a temperature and pressure to form an intermediate overhead stream comprising water, formaldehyde and methanol; and (b) passing said intermediate overhead stream to a formaldehyde separation column operated at a temperature and pressure to enable a stream having a higher formaldehyde concentration than the formaldehyde concentration in the intermediate overhead stream to be formed and recovered from at or near the bottom of the formaldehyde separation column as a formaldehyde enriched stream.

At least a portion of the formaldehyde enriched stream will generally be returned to the reactor in which the acrylic acid is produced. Generally the formaldehyde fed back to the aldol reactor will generally require a particular formaldehyde to water ratio to meet the aldol reactor requirements. Where saturated or unsaturated carboxylic acid is present in the formaldehyde enriched stream its presence is not deleterious as it will be returned to the aldol reactor and so is not lost to the system.

The intermediate overhead stream will have any suitable composition. Water will generally comprise the major portion of the stream. The stream may additionally include acetic acid.

The separation of formaldehyde can be achieved by taking advantage of the reversible formation of formaldehyde oligomers in aqueous solutions at low temperatures. This behaviour makes the apparent volatility of water higher than the apparent volatility of the formaldehyde at low temperatures such as at about 60° C. to about 80° C. At high temperatures, such as at about 120° C. to about 150° C., formaldehyde has a higher volatility than water. This behaviour allows a pressure swing system to separate water from formaldehyde with advantageous lower energy input by operating well away from the pinched areas of the equilibrium curve.

The formaldehyde separation column will be operated under any suitable conditions. Generally it is run under vacuum, such as from about 0.2 bara to about 0.8 bara, in order to allow the water to boil out of the formaldehyde stream which can then be recycled. This reduces the heat load. The pressure used is generally determined by two limits. At the higher end it must be sufficiently low that the temperature is low enough to allow oligomers to form. At the lower end it must be sufficiently high to allow the temperature to be high enough to prevent excessive oligomerisation and hence solid formation. Suitable temperatures for the aldehyde separation column include temperatures in the region of about 60° C. to about 80° C.

One benefit of the use of the formaldehyde recovery column of the present invention, is that any saturated carboxylic acid which has slipped to the formaldehyde recovery column from the first separation column is recovered and recycled in the formaldehyde stream taken from the bottom of the column and returned to the aldol condensation reactor and is therefore not lost to the system.

Without wishing to be bound by any theory, it is believed that a further benefit of the use of the formaldehyde recovery column is that Cannizzaro reactions are supressed. The Cannizzaro reaction results in the formation of methanol and formic acid. The suppression of this reaction is beneficial since, although it is reversible, the methanol formed is more volatile than water and formic acid is less volatile than water. In the water stripping column of the present invention, they will be separated making their recombination impossible. Thus unless the Cannizzaro reactions are supressed they result in a loss of feedstock to the system.

The water separated from the aldehyde in the formaldehyde separation column may be passed to a water stripping column. This column may be operated at any suitable conditions. In one arrangement, it may be run at a pressure of from about 3 to about 6 bara. The pressure limits are determined by requiring sufficient temperature to break down the aldehyde while avoiding losses to formic acid. The feed to the water stripping column is generally removed as overhead from the formaldehyde separation column.

In the water stripping column the water stream is distilled at a higher temperature to that used in the formaldehyde separation column. For example, the stripping column may be operated at a temperature of from about 120° C. to about 150° C. This enables any remaining oligomers to be broken down to the aldehyde monomers which can be recovered in the overheads from the stripping column. These may be returned to the aldehyde separation column. By this means the energy cost of achieving relatively clean water is reduced.

Heat integration may be provided between the water stripping column and the formaldehyde separation column. In one arrangement, the overhead from the water stripping column may be used to provide heat to a reboiler on the formaldehyde column thereby improving the economics of the formaldehyde recovery.

The crude product stream passed to the first separation column may be passed directly from the reactor in which the aldol condensation occurred or it may have been subjected to some pre-separation provided that the product stream passed to the first separation column comprises the unsaturated carboxylic acid, aldehyde, saturated carboxylic acid, and water. Heavy by-products may additionally be present. By 'heavy by-products' we mean by-products having a molecular weight that is greater than that of the unsaturated carboxylic acid. Where the unsaturated carboxylic acid is acrylic acid, the heavy by-products may comprise one or both of maleic acid and methyl acetate.

Before being supplied to the first separation column, the crude product stream may be cooled from the temperature at which it was recovered from the aldol condensation reactor. However this cooling does not reduce the temperature of the stream to below its dew point such that it remains in the vapour phase. Where the crude product stream is subjected to cooling it may be cooled against incoming feed to the aldol condensation reactor such that the feed to the reactor is heated. By this means energy consumption of the combined reaction and separation is reduced.

The crude product stream may be supplied to any suitable point of the first separation column. Generally it will be provided in a lower portion of the column.

The first separation column may be of any configuration but will generally comprise a condenser to allow reflux but will not comprise a reboiler. The absence of a reboiler reduces the risk of polymerisation occurring within the first separation column.

The first separation column may be operated at any suitable conditions. It will generally be operated at about atmospheric pressure or at above atmospheric pressure. The first separation column will generally be operated at a pressure of from about 1.0 bara to about 1.5 bara. Particular advantages may be achieved when operating at a pressure of about 1.2 bara. It will be understood that the actual pressure selected will be determined by hydraulic considerations. A lower pressure in the first separation column will generally be preferred since it allows the use of a lower pressure in the aldol condensation reactor. For example, the use of the pressures detailed above may enable a pressure of about 1.3 bara or about 1.4 bara.

The operating temperature of the first separation column will be a direct function of the feed composition. However, it will generally be operated such that the column bottoms will be from about 110° C. to about 150° C.

The first separation column will usually comprise a vent. This vent will generally require abatement before it can be emitted or recycled. Sufficient pressure will therefore generally be required within the first separation column to allow this abatement. Any suitable means of abatement may be used. Examples of suitable methods include a water wash, catalytic oxidation, or a combination of a water wash with catalytic oxidation.

Without wishing to be bound by any theory, it is believed that in the first separation column the non-condensable vapours present in the crude product stream, which are generally present in excess, provide a stripping medium.

The recovery of the acrylic acid in the crude product stream can be provided by any suitable means. In one arrangement an intermediate product stream comprising acrylic acid, a portion of the water from the feed stream, optionally some acetic acid and heavy by-products where present may be recovered from a first separation column. This intermediate product stream may be passed to a second separation column operated at a temperature and pressure such that the unsaturated carboxylic acid product is separated and recovered.

Allowing water to be present in the intermediate product stream recovered from the first separation column and passed to the second separation column, allows enhanced separation of the unsaturated carboxylic acid from the saturated carboxylic acid than is achievable using conventional methods. Classically the presence of water in the stream recovered from a first separation column would be avoided since its presence would constitute an additional light component and hence it would be expected to increase the heat duty required for the separation. However, the strong interaction between the acetic acid and the water enables the water to act as an entrainer in the separation between the acrylic acid and the acetic acid. This has the effect of reducing column duties. This effect may be as much as about 7%, about 8%, about 9% or about 10% on a feed mass basis.

Separation occurs within the first separation column such that a stream including the desired product and which has a lower concentration of other components than the crude product stream can be recovered. Since this stream requires further purification it is referred to as an 'intermediate' product stream. This stream comprises unsaturated carboxylic acid, a portion of the water from the feed stream, a portion of the saturated carboxylic acid and heavy by-products where present. Any suitable amount of water may be present in this intermediate product stream but it will generally be selected such that it does not create a significant burden on subsequent water separation. Generally, the amount of water present will be from about 1 wt % to about 16 wt %. Some advantages may be noted at a water content in the region of about 6 wt % to about 10 wt %. In one arrangement, the water content may be in the region of about 8 wt %.

The intermediate product stream obtained in the first separation column may be removed from any suitable point. Generally, it will be removed from at or near the bottom of the first separation column.

Additionally, an intermediate side draw stream may be recovered from the first separation column. This side draw stream will generally comprise the saturated carboxylic acid but will generally also comprise some unsaturated carboxylic acid and water.

Where the intermediate product stream recovered from the first separation column is passed to the second separation column, it will generally be passed directly to the second separation column. However, it will be understood that it may be subjected to an alteration in temperature and/or an intermediate separation step before being passed to the second separation column.

Any suitable configuration of second separation column may be used. Generally the second separation column will include both a condenser to allow reflux and a reboiler.

The second separation column will be operated at any suitable operating conditions. As there is a risk of polymerisation within the second separation column, it may be operated at a vacuum to reduce the temperature such that the risk of polymerisation is reduced. A pressure of from about 0 bara to about 1 bara may be used. In some arrangements the pressure will be typically in the region of from about 0.5 bara to 0.6 bara.

Desirable temperatures will depend on the unsaturated carboxylic acid present but generally temperatures of about 160° C. or below, or about 140° C. or below are useful. At these temperatures the risk of polymerisation is reduced.

A polymerisation inhibitor may be added to the second separation column. Any suitable inhibitor may be used. Suitable inhibitors include diphenylamine or its derivatives, hydroquinone or hydroquinone monomethylether, nitroso compounds such as 2-methyl-2-nitrosopropane, nitrosobenzene, and 4-nitrosophenol.

The acrylic acid product is generally recovered in a side draw taken from near the bottom of the second separation column. Thus, for example, in a column having 48 trays, the side draw would be taken from around tray 45 (the trays being numbered from the top of the column). This side draw may be taken as a vapour or liquid stream. The product concentration of the acrylic acid is generally suitable for crystallisation and may be in the region of about 97 mole % or above, about 98 mole % or above, or even about 99 mole % or above. This process stream can then be subjected to crystallisation to allow recovery of the acrylic acid. Generally, the process is suitable for crystallisation to form glacial acrylic acid in a downstream process.

A bottom stream will generally also be removed from the second separation column. This stream will comprise any heavy by-products that were present in the crude product stream fed to the first separation column and/or any oligomers which they have been formed during distillation.

A second column overhead stream will generally also be removed from the second separation column. This stream will comprise acetic acid and water.

The second column overhead stream may be passed to a third separation zone. This zone may comprise two separation zones, an acetic acid separation zone and an entrainer stripper zone where required. It will be understood that the separation zones may be located in the same or different columns. In general, the separation carried out in the third separation zone utilises an entrainer. In addition to facilitating separation, the presence of the entrainer reduces heat duties.

Where two separation zones are present, the stream comprising acetic acid and water recovered as overhead from the second separation zone is fed to the acid separation zone. It may be supplied to any suitable position. The acetic acid separation zone may be of any suitable configuration and will be operated under any suitable conditions to enable separation to occur. Whilst any suitable conditions may be used, the acetic acid separation zone may be operated at a pressure of about 2 bara and a temperature of about 150° C.

The intermediate side draw stream from the first separation column may be treated separately but will generally be treated with the second separation column overhead stream in the third separation zone. These streams can be combined before being fed to the acid separation zone or they may be added separately to the separation zone.

Any acrylic acid carried over in the second column overhead stream may be recovered from the acid separation column as an acid separation bottom stream and recycled to the second separation column.

In the event that any acetic acid has been carried over in the second column overhead stream this may be recovered as a side draw. This can be recycled to the aldol condensation reactor. Any water which may be present in this side draw recycle stream is not problematic since water can be included in the feed to the aldol condensation reactor.

The presence of the entrainer in the acrylic acid separation zone will generally ensure good recovery of the acetic acid. This is desirable since any acrylic acid which slips to the entrainer stripper zone is lost from the flowsheet and will be a contaminant to water.

Any suitable entrainer may be used. Examples of suitable entrainers include isopropyl acetate, ethyl propionate, hexyl acetate, 2-methyl hexanone-5, diisobutyl ketone, hexyl formate, 2-octanone, 4-methyl-2-pentanone, diethyl malonate, 2-undecanone, 2,4-pentanedione, propiophenone, 4-methyl pentyl acetate, ethyl n-valerate, amyl propionate, propyl caproate, ethylene glycol diacetate, triacetin, isophorone, methyl-t-butyl ether, acetal, tetrahydrofuran, nitromethane, acetaldehyde oxime, propyl formate and 2,3-butanediol with isopropyl acetate offering particular advantages.

It is desirable that the selected entrainer is immiscible with water such that it can be readily separated therefrom. In this arrangement, in a condenser of the acetic acid separator zone two liquid phases can be formed. The entrainer-rich phase can be decanted and refluxed back to the separation zone. In one arrangement a portion of the entrainer-rich phase may be returned to a lower point in the acetic acid separation zone.

A water-rich stream recovered from the acetic acid separator zone is passed to the entrainer stripper zone in which any entrainer which is retained in the water stream, usually as an azeotrope, can be separated. In one arrangement two liquid phases are formed in the condenser associated with the stripper with the entrainer rich phase being separated by being decanted and optionally returned to the acetic acid separator zone. The water phase will generally be refluxed to the entrainer separator zone.

In one arrangement, the overheads from the acetic acid separator zone and the entrainer separator zone may be combined such that a single decanter arrangement may be used.

Figure 2:
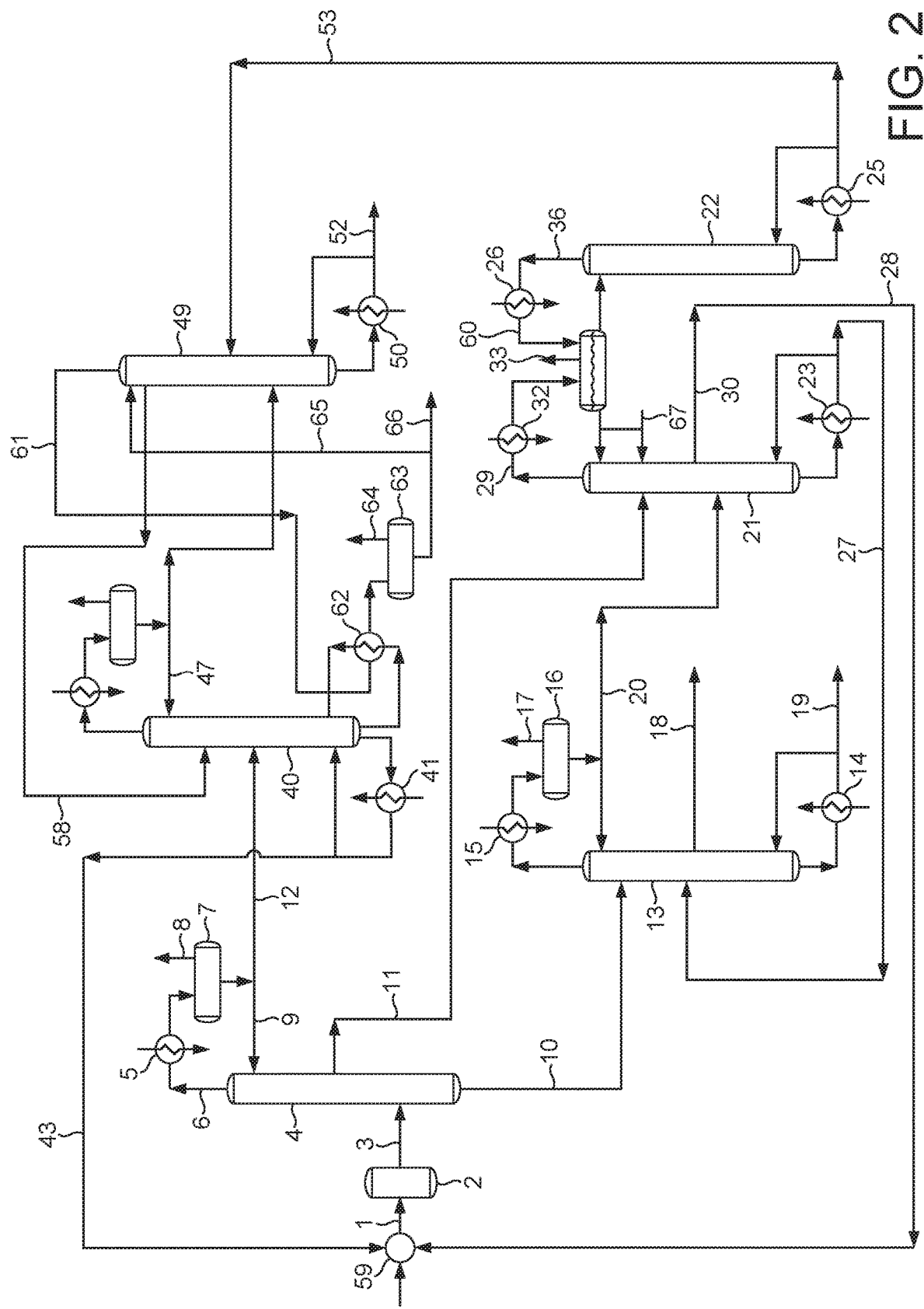

The present invention will now be described, by way of example, with reference to the accompanying figures in which:

FIG. 1 is a schematic diagram of one aspect of the process of the present invention; and FIG. 2 is a schematic diagram of the process of a second aspect of the present invention.

It will be understood by those skilled in the art that the drawings are diagrammatic and that further items of equipment such as reflux drums, pumps, vacuum pumps, compressors, gas recycle compressors, temperature sensors, pressure sensors, pressure relief valves, control valves, flow controllers, level controllers, and the like may be required in a commercial plant. The provision of such ancillary items of equipment forms no part of the present invention and is in accordance with conventional chemical engineering practice.

As shown in FIG. 1 feed is fed in line 1 to an aldol condensation reactor 2 where reaction occurs. The product stream is cooled in the cooling equipment (not shown) of the reactor 2 before being fed in line 3 to the first separation column 4. The feed which will be in the vapour phase will comprise formaldehyde, water, acetic acid, and acrylic acid. Heavy by-products, nitrogen and other non-condensable vapours, and methanol will also generally be present.

The first separation column 4 does not include a reboiler. However, an overhead condenser 5 is present. The first separation column 4 uses the nitrogen and other non-condensibles to provide the stripping medium. An overhead stream 6 from the first separation column 4 having been passed through the condenser 5 may be passed to a vapour/liquid separator 7 where gases can be vented in line 8. Separated liquid can be returned in line 9 to the first separation column 4 as reflux.

The first separation column 4 is operated such that three streams are formed. An intermediate product stream 10 is recovered from at or near the bottom of the first separation column 4. An intermediate side draw stream 11 is recovered optionally from a point above the point at which the feed to the first separation column 4 is added. This side draw stream will generally comprise the acetic acid, some acrylic acid and water. An intermediate overhead stream 12 comprising formaldehyde and water is also recovered. Acetic acid and methanol may also be present.

The intermediate product stream 10 is passed to the second separation column 13. In this example the second separation column 13 includes both a reboiler 14 and a condenser 15. A vapour/liquid separator 16 may be present after the condenser such that any gas present can be separated and vented in line 17. A polymerisation inhibitor may be added to this separation column 13 at any suitable point, not shown. The product acrylic acid is recovered as a side draw 18. A bottom stream 19 may be recovered from the second separation column 13. This will comprise any heavies including byproducts and oligomers.

An overhead stream 20 from the second separation column 13 will comprise acetic acid and water. This is passed to the third separation zone which comprises an acid separation zone which is column 21 and an entrainer stripping zone which is column 22. The acid separation column 21 is provided with reboiler 23 and condenser 24. The entrainer stripping column 22 is provided with reboiler 25 and condenser 26.

The intermediate side draw 11 from the first separation column 4 may also be fed to the acid separation column 21.

An entrainer is supplied to the acid separation column 21 in stream 31 where it is combined with recycled entrainer before being supplied to the column 21 in stream 32.

Any acrylic acid which has been fed to the acid separation column 21 is separated as columns bottom stream 27 which may be recycled to the second separation column 13.

Acetic acid separated in acid separation column 21 is removed as a side draw in stream 28 and returned to the aldol condensation reactor 2 via mixer 59. Acid separation column 21 overhead 29 is cooled in condenser 24 before being passed to decanter 30. Any non-condensed gases are removed in vent 33. Since the entrainer is immiscible with water, two liquid phases are formed and these can be separated in decanter 30. An entrainer-rich stream 34 is returned to column 21 as reflux.

A water-rich stream recovered from the decanter 30 is passed in stream 35 to the entrainer stripping column 22. The overhead stream 36 from column 22 is passed to condenser 26 and then to decanter 37. Any non-condensed gases are removed in vent 38. In decanter 37 two liquid phases are separated with an entrainer rich stream being returned in line 39 to the acid separation column 21. The other liquid phase is returned to the entrainer stripping column 22 as reflux.

The intermediate overhead stream 12 which comprises water, formaldehyde, acetic acid and methanol is fed to the aldehyde recovery column 40. The aldehyde recovery column 40 is provided with a reboiler 41 and a condenser 42. Formaldehyde recovered from the bottom of the aldehyde recovery column 40 is recycled in stream 43 to the aldol condensation reactor 2 via mixer 59.

Overhead stream 44 having been passed through condenser 42 is passed to vapour/liquid separator 45. Any gases can be separated and removed in vent 46. A portion of the liquid is returned in line 47 to the aldehyde recovery column 40 as reflux. The remainder is passed in stream 48 to a water stripping column 49. The bottom stream from entrainer stripping column 22 may also be fed to this water stripping column in line 53. In this column the water is separated from any residual formaldehyde. The water stripping column includes a reboiler 50 and a condenser 51. Water is recovered from the bottom of the column in stream 52. The separated formaldehyde is removed as overhead in stream 54. It is then cooled in condenser 51 and then passed to vapour/liquid separator 55. Any separated gas can be removed in vent 56. A portion of the liquid can be returned to the water stripping column in line 57 as reflux. The remainder is returned to the aldehyde recovery column in line 58.

Modifications of the process illustrated in FIG. 1 are illustrated in FIG. 2. Whilst these modifications are discussed in combination, it will be understood that one or more of them may be used.

In general the process of FIG. 1 is the same as that of FIG. 2 and the same items are given the same reference numerals. As illustrated in FIG. 2, the overhead stream 36 from the entrainer stripping column 22, having been passed through condenser 26, rather than being passed to decanter 37 of FIG. 1, is passed to decanter 30 in line 60 where it is combined with the overhead stream from the acid separation column 21.

In the arrangement of FIG. 2, there is heat integration between the water stripping column 49 and the aldehyde recovery column 40. In this arrangement, the overhead stream 61 from the water stripping column 49 is used to provide heat in reboiler 62 to the aldehyde recovery column 40. Having been passed through reboiler 62, the stream is passed to a decanter 63 which may include a vent 64. Reflux is provided to the water stripping 49 via line 65. Methanol may be recovered in line 66. Recovered formaldehyde may be returned to the formaldehyde recovery column 40 in line 58.

The addition of the entrainer in line 67 to the acid separation zone 21 is illustrated in FIG. 2.

The present invention will now be described by way of example with reference to the following examples.

EXAMPLE 1

The following example demonstrates the advantages associated with the pressure swing in the formaldehyde recovery zone.

In this example, the desired end product from the formaldehyde recovery zone is a recyclable stream with a fixed formaldehyde to water ratio of 0.9:1 by mass. The other target product from the formaldehyde recovery zone is a stream containing 99.9% by mole water, suitable for waste treatment. This is to be achieved from two streams containing water, acetic acid and formaldehyde.

|  | Stream 1 | Stream 2 |
| --- | --- | --- |
| Water | 0.769 | 0.971 |
| Formaldehyde (equivalent) | 0.189 | 0.027 |
| Acetic | 0.041 | 0.002 |
| Dissolved lights | 0.001 | — |

The columns are simulated in Aspen Plus 8.4, using UNIFAC group methods with the Hayden-O'Connell vapour phase correction, and apparent components using equilibrium chemistry to account for the formation of multiple formaldehyde-derived components.

COMPARATIVE EXAMPLE 1

In this comparative example, a single column separation, where the column has 90 theoretical stages, a reboil duty of 20 MW, and a condenser pressure of 5 bar absolute is used. The aim is to recover a formaldehyde-rich product is recovered as an overhead stream. The residue stream is only 95.3% water by mole, the remainder comprising primarily acetic with some formaldehyde. Formaldehyde recovery of this column is 97.8%

COMPARATIVE EXAMPLE 2

In this comparative example, a further single column separation, where the column has 90 theoretical stages, and a condenser pressure of 0.2 bar absolute. The column achieves a formaldehyde recovery of 99.7%. Furthermore, the water stream is 99.7% pure, with the remainder formaldehyde. The acetic content of the feed is recovered to the formaldehyde rich product, in which it can be recycled to the reactor. However, the reboil duty required to achieve this is 27 MW. The practical design of this column would be challenging, due to the low pressure drop requirements.

EXAMPLE 3

The present invention overcomes the disadvantages with the prior art. In this example, two columns are used. The first column has 50 theoretical stages and stream 1 is fed to it. The first column also has a condenser pressure of 0.2 bar absolute. The second column has 40 theoretical stages and stream 2 is fed to it. The second column has a condenser pressure of 5 bar absolute. In this case, 99.7% recovery of formaldehyde is again achieved. Similarly, the acetic acid is recovered for recycle in the formaldehyde-rich stream. However, the purity of the water stream is 99.9% by mole. Furthermore, the duty of the first column is 14.3 MW and the duty of the second column is 5.4 MW, giving an overall duty of 19.7 MW, which is lower than the two comparative examples. Lastly, the condenser temperature of the second column is sufficient to provide duty to the first column, giving a net duty requirement after heat integration as low as 10 MW.

EXAMPLES 4-5

The following examples demonstrate the use of water as an entrainer in the acetic acid and water separation zone, specifically the acetic acid/acrylic acid separation step.

For both examples, a column of 48 theoretical stages is modelled in Aspen Plus 8.4. The condenser pressure is 0.4 bar absolute. The column removes acrylic product as a side-draw at 99% by mol purity and 97% recovery.

COMPARATIVE EXAMPLE 4

The feed stream composition is as follows:

| Mol fractions | Stream 3 |
| --- | --- |
| Water | — |
| Formaldehyde | 0.009 |
| Acrylic Acid | 0.572 |
| Acetic Acid | 0.415 |
| Maleic Acid | 0.004 |

In this example, the reboil duty needed to achieve the specified separation is 2972 kJ/kg of acrylic product.

EXAMPLE 5

The feed stream composition is as follows:

| Mol fractions | Stream 3 |
| --- | --- |
| Water | 0.150 |
| Formaldehyde | 0.007 |
| Acrylic Acid | 0.486 |
| Acetic Acid | 0.353 |
| Maleic Acid | 0.004 |

In this example, the reboil duty needed to achieve the specified separation is 2704 kJ/kg of feed.

Thus the reboil duty required where water is allowed to slip into an intermediate product stream is substantially reduced when compared to the arrangement where it is removed.

The invention claimed is:

1. A process for purification of a crude product stream recovered from the production of acrylic acid by an aldolisation reaction, said product stream comprising acrylic acid, formaldehyde, water, non-condensable vapours and optionally heavy by-products; said process comprising:
    (a) providing the crude product stream in the vapour phase to a first separation column operated at a temperature of about 110° C. to about 150° C. and at a pressure of about 1.0 bara to about 1.5 bara to form an intermediate overhead stream comprising water, formaldehyde and methanol; and
    (b) passing said intermediate overhead stream to a formaldehyde separation column operated at a temperature at a temperature of from about 60° C. to about 80° C. and at a pressure of from about 0.2 bara to about 0.8 bara to enable a stream having a higher formaldehyde concentration than the formaldehyde concentration in the intermediate overhead stream to be formed and recovered from at or near the bottom of the formaldehyde separation column as a formaldehyde enriched stream.

2. The process according to claim 1 wherein a water stream recovered from the formaldehyde separation column is passed to a water stripping column.

3. The process according to claim 2 wherein the water stripping column is operated at a pressure of from about 3 to about 6 bara.

4. The process according to claim 2 wherein the water stripping column is operated at a temperature of from about 120° C. to about 150° C.

5. The process according to claim 2 wherein heat integration is provided between the water stripping column and the formaldehyde separation column.

6. The process according to claim 5 wherein an overhead from the water stripping column is used to provide heat to a reboiler on the formaldehyde recovery column.

* * * * *